(12) United States Patent
White et al.

(10) Patent No.: US 7,615,061 B2
(45) Date of Patent: Nov. 10, 2009

(54) BONE ANCHOR SUTURE-LOADING SYSTEM, METHOD AND APPARATUS

(75) Inventors: George W. White, Corona, CA (US); Francis Vijay, Irvine, CA (US)

(73) Assignee: ArthroCare Corporation, Austin, TX (US)

( * ) Notice: Subject to any disclaimer, the term of this patent is extended or adjusted under 35 U.S.C. 154(b) by 0 days.

(21) Appl. No.: 11/365,266

(22) Filed: Feb. 28, 2006

(65) Prior Publication Data

US 2007/0203508 A1 Aug. 30, 2007

(51) Int. Cl.
*A61B 17/04* (2006.01)
*A61B 17/84* (2006.01)
*D03J 3/00* (2006.01)

(52) U.S. Cl. .............. 606/148; 606/232; 606/300; 289/17

(58) Field of Classification Search .......... 606/72, 606/148, 225, 232, 74, 103, 300; 289/17
See application file for complete search history.

(56) References Cited

U.S. PATENT DOCUMENTS

| | | | |
|---|---|---|---|
| 918,570 A | 4/1909 | Mather | 292/318 |
| 919,138 A | 4/1909 | Drake et al. | 606/144 |
| 1,153,053 A | 9/1915 | Forster | 43/44.85 |
| 1,565,041 A | 12/1925 | Arneu | 24/129 R |
| 2,269,963 A | 1/1942 | Wrapler | 604/604 |
| 2,286,578 A | 6/1942 | Sauter | 606/144 |
| 2,485,531 A | 10/1949 | Dzus et al. | 128/92 |
| 2,600,395 A | 6/1952 | Domoj et al. | 87/13 |
| 3,143,916 A | 8/1964 | Rice | 85/71 |
| 3,942,407 A | 3/1976 | Mortensen | 85/71 |
| 3,946,740 A | 3/1976 | Bassett | 128/334 |
| 3,994,521 A | 11/1976 | Van Gompel | 292/319 |
| 4,047,533 A | 9/1977 | Perciaccante et al. | 128/335.5 |
| 4,109,658 A | 8/1978 | Hughes | 128/340 |
| 4,164,225 A | 8/1979 | Johnson et al. | 128/334 |
| 4,186,921 A | 2/1980 | Fox | 29/461 |
| 4,210,148 A | 7/1980 | Stivala | 606/232 |
| 4,217,375 A | 8/1980 | Adams | 427/85 |
| 4,274,324 A | 6/1981 | Giannuzzi | 411/38 |

(Continued)

FOREIGN PATENT DOCUMENTS

DE 025 32 242 A1 2/1977

(Continued)

OTHER PUBLICATIONS

PCT Search Report and Written Opinion for PCT/US06/20657 7 pgs, Mailed Oct. 2, 2007.

(Continued)

*Primary Examiner*—Julian W Woo
*Assistant Examiner*—Melissa Ryckman
(74) *Attorney, Agent, or Firm*—Matthew Scheele; Brian Szymczak

(57) ABSTRACT

A suture-loading system, method and apparatus for loading a suture onto a bone anchor, the system comprising: a bone anchor comprising a suture leg-anchoring structure and a plurality of body holes on the anchor; a suture comprising a standing end portion and a working end portion; a standing end trackway to guide the standing end portion of the suture through the suture leg-anchoring structure; and a working end trackway to guide the working end portion of the suture through the body holes in the anchor.

19 Claims, 9 Drawing Sheets

U.S. PATENT DOCUMENTS

| | | | |
|---|---|---|---|
| 4,301,551 A | 11/1981 | Dore et al. .................. 623/13.3 |
| 4,319,428 A | 3/1982 | Fox ................................. 47/42 |
| 4,345,601 A | 8/1982 | Fukuda ....................... 128/339 |
| 4,373,530 A | 2/1983 | Kilejian .................. 128/334 R |
| 4,384,389 A | 5/1983 | Sato .......................... 24/136 K |
| 4,392,915 A | 7/1983 | Zajac .......................... 156/643 |
| 4,409,974 A | 10/1983 | Freedland ...................... 128/92 |
| 4,456,270 A | 6/1984 | Zettl et al. ...................... 279/62 |
| 4,467,478 A | 8/1984 | Jurgutis ....................... 606/75 |
| 4,483,023 A | 11/1984 | Hoffman, Jr. et al. .... 623/13.15 |
| 4,493,323 A | 1/1985 | Albright et al. ............. 128/340 |
| 4,513,021 A | 4/1985 | Purdes et al. .................. 427/38 |
| 4,537,795 A | 8/1985 | Nath et al. ..................... 427/39 |
| 4,545,327 A | 10/1985 | Campbell et al. ........... 118/719 |
| 4,590,928 A | 5/1986 | Hunt et al. ..................... 606/72 |
| 4,597,776 A | 7/1986 | Ullman et al. ............. 48/197 R |
| 4,605,414 A | 8/1986 | Czajka ..................... 623/13.11 |
| 4,621,640 A | 11/1986 | Mulhollan et al. .......... 128/340 |
| 4,633,809 A | 1/1987 | Hirose et al. ................ 118/719 |
| 4,635,637 A | 1/1987 | Schreiber .................... 128/337 |
| 4,640,221 A | 2/1987 | Barbee et al. ............... 118/689 |
| 4,657,461 A | 4/1987 | Smith .......................... 411/340 |
| 4,672,957 A | 6/1987 | Hourahane ................... 606/80 |
| 4,712,542 A | 12/1987 | Daniel et al. .................. 606/96 |
| 4,716,852 A | 1/1988 | Tsujii et al. ................. 118/720 |
| 4,721,103 A | 1/1988 | Freedland ...................... 128/92 |
| 4,731,084 A | 3/1988 | Dunn et al. ................ 623/13.19 |
| 4,738,255 A | 4/1988 | Goble et al. ............ 128/92 YF |
| 4,738,748 A | 4/1988 | Kisa ............................. 156/643 |
| 4,741,330 A | 5/1988 | Hayhurst ................... 123/43 R |
| 4,750,492 A | 6/1988 | Jacobs ......................... 606/230 |
| 4,772,286 A | 9/1988 | Goble et al. ............... 623/13.14 |
| 4,779,616 A | 10/1988 | Johnson et al. ............. 606/148 |
| 4,781,182 A | 11/1988 | Purnell et al. .................. 128/92 |
| 4,792,336 A | 12/1988 | Hlavacek et al. ......... 623/13.18 |
| 4,809,408 A | 3/1989 | Abrahamson ............. 24/136 K |
| 4,823,780 A | 4/1989 | Odensten et al. .............. 606/96 |
| 4,828,439 A | 5/1989 | Giannuzzi ..................... 411/37 |
| 4,834,755 A | 5/1989 | Silvestrini et al. ........ 623/13.19 |
| 4,836,205 A | 6/1989 | Barrett ........................ 128/340 |
| 4,851,005 A | 7/1989 | Hunt et al. ..................... 623/18 |
| 4,870,957 A | 10/1989 | Goble et al. ................... 606/73 |
| 4,910,043 A | 3/1990 | Freeman et al. ............... 427/39 |
| 4,917,700 A | 4/1990 | Aikins ..................... 623/13.19 |
| 4,923,461 A | 5/1990 | Caspari ....................... 606/146 |
| 4,926,860 A | 5/1990 | Stice et al. .................. 606/144 |
| 4,935,027 A | 6/1990 | Yoon ........................... 606/146 |
| 4,946,467 A | 8/1990 | Ohi et al. .................... 606/228 |
| 4,946,468 A | 8/1990 | Li ................................ 606/232 |
| 4,957,498 A | 9/1990 | Caspari ....................... 606/146 |
| 4,962,929 A | 10/1990 | Melton, Jr. .................. 473/516 |
| 4,968,315 A | 11/1990 | Gatturna ....................... 606/72 |
| 4,981,149 A | 1/1991 | Yoon ........................... 128/898 |
| 4,987,665 A | 1/1991 | Dumican ....................... 28/218 |
| 5,002,550 A | 3/1991 | Li ................................ 606/139 |
| 5,019,093 A | 5/1991 | Kaplan et al. ............... 606/228 |
| 5,037,422 A | 8/1991 | Hayhurst ....................... 606/72 |
| 5,046,513 A | 9/1991 | Gatturna ..................... 128/898 |
| 5,059,201 A | 10/1991 | Asnis .......................... 606/144 |
| 5,062,344 A | 11/1991 | Gerker ............................. 87/8 |
| 5,085,661 A | 2/1992 | Moss ........................... 606/139 |
| 5,147,166 A | 9/1992 | Harker ......................... 411/29 |
| 5,195,542 A | 3/1993 | Gazielly et al. ............... 60/244 |
| 5,203,787 A | 4/1993 | Noblitt et al. ............... 606/232 |
| RE34,293 E | 6/1993 | Goble et al. |
| 5,217,495 A | 6/1993 | Kaplan et al. ............. 623/13.18 |
| 5,219,359 A | 6/1993 | McQuilkin et al. .......... 606/232 |
| 5,222,977 A | 6/1993 | Esser ........................... 606/223 |
| 5,224,946 A | 7/1993 | Hayhurst ....................... 606/72 |
| 5,258,016 A | 11/1993 | DiPoto et al. ................ 606/232 |
| 5,259,846 A | 11/1993 | Granger et al. .............. 606/224 |
| 5,263,984 A | 11/1993 | Li ............................ 623/13.18 |
| 5,275,176 A | 1/1994 | Chandler ..................... 606/242 |
| 5,275,976 A | 1/1994 | Moslehi ....................... 438/800 |
| 5,304,184 A | 4/1994 | Hathaway et al. ........... 606/144 |
| 5,304,279 A | 4/1994 | Coultas et al. ......... 156/345.49 |
| 5,312,422 A | 5/1994 | Trott ............................ 606/144 |
| 5,318,575 A | 6/1994 | Chesterfield et al. ........ 606/151 |
| 5,324,308 A | 6/1994 | Pierce ......................... 606/232 |
| 5,326,205 A | 7/1994 | Anspach, III et al. ......... 411/43 |
| 5,330,442 A | 7/1994 | Green .......................... 606/232 |
| 5,330,468 A | 7/1994 | Burkhart ....................... 606/96 |
| 5,330,488 A | 7/1994 | Goldrath ..................... 606/148 |
| 5,336,240 A | 8/1994 | Metzler ....................... 606/232 |
| 5,338,363 A | 8/1994 | Kawata et al. ............... 118/725 |
| 5,354,298 A | 10/1994 | Lee et al. ....................... 606/72 |
| 5,356,120 A | 10/1994 | Konig et al. ................. 266/175 |
| 5,364,407 A | 11/1994 | Poll .............................. 606/139 |
| 5,366,585 A | 11/1994 | Robertson et al. ........... 156/643 |
| 5,376,118 A | 12/1994 | Kaplan et al. ............. 623/23.72 |
| 5,383,905 A | 1/1995 | Gold et al. ................... 606/232 |
| 5,397,325 A | 3/1995 | Della Badia et al. ......... 606/144 |
| 5,405,352 A | 4/1995 | Weston ........................ 606/148 |
| 5,405,359 A | 4/1995 | Pierce ......................... 606/232 |
| 5,409,494 A | 4/1995 | Morgan ......................... 606/96 |
| 5,413,579 A | 5/1995 | Tom Du Toit ................. 606/87 |
| 5,417,691 A | 5/1995 | Hayhurst ....................... 606/72 |
| 5,417,699 A | 5/1995 | Klein et al. .................. 606/139 |
| 5,417,712 A | 5/1995 | Whittaker et al. ........... 606/232 |
| 5,431,666 A | 7/1995 | Sauer et al. .................. 606/139 |
| 5,441,508 A | 8/1995 | Gazielly et al. .............. 606/151 |
| 5,445,167 A | 8/1995 | Yoon et al. .................. 128/898 |
| 5,450,860 A | 9/1995 | O'Connor .................... 606/224 |
| 5,453,124 A | 9/1995 | Moslehi et al. ................ 18/715 |
| 5,454,823 A | 10/1995 | Richardson et al. ......... 606/148 |
| 5,464,427 A | 11/1995 | Curtis et al. ................. 606/232 |
| 5,468,298 A | 11/1995 | Lei et al. ..................... 118/728 |
| 5,470,335 A | 11/1995 | DuToit ......................... 606/73 |
| 5,472,452 A | 12/1995 | Trott ............................ 606/232 |
| 5,474,565 A | 12/1995 | Trott ............................ 606/144 |
| 5,480,403 A | 1/1996 | Lee et al. ....................... 606/72 |
| 5,486,197 A | 1/1996 | Le et al. ...................... 606/232 |
| 5,499,991 A | 3/1996 | Garman et al. .............. 606/148 |
| 5,500,256 A | 3/1996 | Watabe ........................ 427/579 |
| 5,501,683 A | 3/1996 | Trott ............................ 606/72 |
| 5,501,695 A | 3/1996 | Anspach, Jr. et al. .......... 606/72 |
| 5,505,735 A | 4/1996 | Li ................................ 606/72 |
| 5,514,159 A | 5/1996 | Matula et al. ................ 606/232 |
| 5,522,820 A | 6/1996 | Caspari et al. ............... 606/148 |
| 5,527,322 A | 6/1996 | Klein et al. .................. 606/144 |
| 5,527,343 A | 6/1996 | Bonutti ........................ 606/232 |
| 5,531,792 A | 7/1996 | Huene ............................ 623/16 |
| 5,532,190 A | 7/1996 | Goodyear et al. ............ 437/225 |
| 5,534,012 A | 7/1996 | Bonutti ........................ 606/232 |
| 5,540,703 A | 7/1996 | Barker, Jr. et al. ........... 606/139 |
| 5,545,180 A | 8/1996 | Le et al. ...................... 606/232 |
| 5,549,617 A | 8/1996 | Green et al. ................. 606/144 |
| 5,549,630 A | 8/1996 | Bonutti ........................ 606/232 |
| 5,553,360 A | 9/1996 | Lucas et al. ................ 24/136 K |
| 5,556,474 A | 9/1996 | Otani et al. .................. 118/723 |
| 5,562,689 A | 10/1996 | Green et al. ................. 606/151 |
| 5,569,305 A | 10/1996 | Bonutti ........................ 606/232 |
| 5,569,306 A | 10/1996 | Thal ............................ 606/232 |
| 5,571,104 A | 11/1996 | Li ................................ 606/72 |
| 5,571,120 A | 11/1996 | Yoon ........................... 606/148 |
| 5,573,540 A * | 11/1996 | Yoon ........................... 606/139 |
| 5,573,542 A | 11/1996 | Stevens ....................... 606/144 |
| 5,573,548 A | 11/1996 | Nazre et al. .................. 606/232 |
| 5,575,801 A | 11/1996 | Habermeyer et al. ........ 606/148 |
| 5,584,835 A | 12/1996 | Greenfield ..................... 606/73 |
| 5,584,839 A | 12/1996 | Gieringer ...................... 606/96 |
| 5,584,860 A | 12/1996 | Goble et al. ................. 606/232 |
| 5,584,862 A | 12/1996 | Bonutti ........................ 606/232 |
| 5,590,387 A | 12/1996 | Schmidt et al. ............... 419/36 |

| | | | | | | | |
|---|---|---|---|---|---|---|---|
| 5,591,207 | A | 1/1997 | Coleman ............... 606/232 | 5,882,340 | A | 3/1999 | Yoon .................. 604/164 |
| 5,593,189 | A | 1/1997 | Little ...................... 289/17 | 5,884,009 | A | 3/1999 | Okase .................. 392/418 |
| 5,601,558 | A | 2/1997 | Torrie et al. ............... 606/72 | 5,885,294 | A | 3/1999 | Pedlick et al. ............ 606/80 |
| 5,609,597 | A | 3/1997 | Lehrer .................. 606/139 | 5,885,751 | A | 3/1999 | Weidman et al. .......... 430/315 |
| 5,611,801 | A | 3/1997 | Songer .................. 606/73 | 5,891,168 | A | 4/1999 | Thal ................... 606/232 |
| 5,613,974 | A | 3/1997 | Andreas et al. ........... 606/144 | 5,893,850 | A | 4/1999 | Cachia .................. 606/72 |
| 5,618,290 | A | 4/1997 | Toy et al. ................ 606/139 | 5,902,311 | A | 5/1999 | Andreas et al. ........... 606/144 |
| 5,618,314 | A | 4/1997 | Harwin et al. ............ 606/232 | 5,904,692 | A | 5/1999 | Steckel et al. ............ 606/139 |
| 5,618,349 | A | 4/1997 | Yuuki .................... 118/715 | 5,911,721 | A | 6/1999 | Nicholson et al. .......... 606/72 |
| 5,626,614 | A | 5/1997 | Hart ..................... 606/232 | 5,921,994 | A | 7/1999 | Andreas et al. ........... 606/144 |
| 5,630,824 | A | 5/1997 | Hart ..................... 606/139 | 5,935,129 | A | 8/1999 | Mdevitt .................. 606/72 |
| 5,632,748 | A | 5/1997 | Beck, Jr. et al. ............ 606/72 | 5,941,900 | A | 8/1999 | Bonutti ................. 606/232 |
| 5,645,552 | A | 7/1997 | Sherts ................... 606/145 | 5,941,901 | A | 8/1999 | Egan .................... 606/232 |
| 5,645,589 | A | 7/1997 | Li ......................... 623/16 | 5,944,724 | A | 8/1999 | Lizardi .................. 606/104 |
| 5,647,874 | A | 7/1997 | Hayhurst ................. 606/72 | 5,944,739 | A | 8/1999 | Zlock et al. .............. 606/232 |
| 5,647,912 | A | 7/1997 | Kaminishizono et al. ... 118/719 | 5,947,982 | A | 9/1999 | Duran ................... 606/139 |
| 5,649,940 | A | 7/1997 | Hart et al. ................ 606/148 | 5,948,000 | A | 9/1999 | Larsen et al. ............. 606/232 |
| 5,658,313 | A | 8/1997 | Thal ..................... 606/232 | 5,948,001 | A | 9/1999 | Larsen .................. 606/232 |
| 5,665,108 | A | 9/1997 | Galindo .................. 606/215 | 5,948,002 | A | 9/1999 | Bonutti ................. 606/232 |
| 5,665,110 | A | 9/1997 | Chervitz et al. ............ 606/232 | 5,957,953 | A | 9/1999 | DiPoto et al. ............. 606/232 |
| 5,665,112 | A | 9/1997 | Thal ..................... 606/232 | 5,957,968 | A | 9/1999 | Belden et al. ............. 607/126 |
| 5,667,528 | A | 9/1997 | Colligan ................. 606/224 | 5,961,530 | A | 10/1999 | Moore et al. .............. 606/148 |
| D385,352 | S | 10/1997 | Bales et al. | 5,961,538 | A | 10/1999 | Pedlick et al. ............ 606/232 |
| 5,674,574 | A | 10/1997 | Atwell et al. .............. 427/561 | 5,968,044 | A | 10/1999 | Nicholson et al. .......... 606/72 |
| 5,681,333 | A | 10/1997 | Burkhart et al. ............ 606/148 | 5,972,430 | A | 10/1999 | DiMeo, Jr. et al. ..... 427/255.32 |
| 5,681,351 | A | 10/1997 | Jamiolkowski et al. ....... 606/232 | 5,980,558 | A | 11/1999 | Wiley ................... 606/232 |
| 5,683,417 | A | 11/1997 | Cooper .................. 606/223 | 5,980,559 | A | 11/1999 | Bonutti ................. 606/232 |
| 5,683,418 | A | 11/1997 | Luscombe et al. .......... 606/232 | 5,983,906 | A | 11/1999 | Zhao et al. ............... 134/1.1 |
| 5,683,419 | A | 11/1997 | Thal ..................... 606/232 | 5,984,933 | A | 11/1999 | Yoon .................... 606/148 |
| 5,690,649 | A | 11/1997 | Li ....................... 606/139 | 5,993,459 | A | 11/1999 | Larsen .................. 606/104 |
| 5,693,060 | A | 12/1997 | Martin .................. 606/148 | 6,001,104 | A | 12/1999 | Benderev et al. ........... 606/80 |
| 5,697,950 | A | 12/1997 | Fucci et al. ............... 606/232 | 6,001,109 | A | 12/1999 | Kontos .................. 606/148 |
| 5,702,397 | A | 12/1997 | Goble et al. ............... 606/72 | 6,007,566 | A | 12/1999 | Wenstrom ............... 606/232 |
| 5,702,398 | A | 12/1997 | Tarabishy ................ 606/72 | 6,007,567 | A | 12/1999 | Bonutti ................. 606/232 |
| 5,707,362 | A | 1/1998 | Yoon .................... 604/164 | 6,010,525 | A | 1/2000 | Bonutti et al. ............. 606/232 |
| 5,707,394 | A | 1/1998 | Miller et al. ............... 606/232 | 6,013,083 | A | 1/2000 | Bennett ................. 606/104 |
| 5,709,708 | A | 1/1998 | Thal ..................... 606/232 | 6,017,346 | A | 1/2000 | Grotz .................... 606/72 |
| 5,720,765 | A | 2/1998 | Thal ..................... 606/232 | 6,022,360 | A | 2/2000 | Reimels et al. ............ 606/144 |
| 5,725,529 | A | 3/1998 | Nicholson et al. .......... 606/72 | 6,022,373 | A | 2/2000 | Li ....................... 606/232 |
| 5,725,541 | A | 3/1998 | Anspach, III et al. ....... 606/151 | 6,024,758 | A | 2/2000 | Thal ................... 606/232 |
| 5,728,136 | A | 3/1998 | Thal ..................... 606/232 | 6,033,430 | A | 3/2000 | Bonutti ................. 606/232 |
| 5,733,307 | A | 3/1998 | Albright et al. ............ 606/232 | 6,036,699 | A | 3/2000 | Andreas et al. ........... 606/139 |
| 5,741,281 | A | 4/1998 | Martin .................. 606/148 | 6,045,571 | A | 4/2000 | Hill et al. ................. 606/228 |
| 5,741,282 | A | 4/1998 | Anspach, III et al. ....... 606/151 | 6,045,572 | A | 4/2000 | Johnson et al. ............ 606/232 |
| 5,746,834 | A | 5/1998 | Hanley .................. 118/715 | 6,045,573 | A | 4/2000 | Wenstrom et al. .......... 606/232 |
| 5,755,886 | A | 5/1998 | Wang et al. ............... 118/715 | 6,045,574 | A | 4/2000 | Thal ................... 606/232 |
| 5,766,250 | A | 6/1998 | Chervitz et al. ............ 623/13 | 6,048,351 | A | 4/2000 | Gordon et al. ............. 606/144 |
| 5,776,150 | A | 7/1998 | Nolan et al. .............. 606/148 | 6,050,506 | A | 4/2000 | Guo et al. ................. 239/558 |
| 5,779,719 | A | 7/1998 | Klein et al. ............... 606/144 | 6,051,006 | A | 4/2000 | Shluzas et al. ............. 606/148 |
| 5,782,863 | A | 7/1998 | Bartlett .................. 606/232 | 6,053,935 | A | 4/2000 | Brenneman et al. ......... 606/232 |
| 5,782,864 | A | 7/1998 | Lizardi .................. 606/232 | 6,056,773 | A | 5/2000 | Bonutti ................. 606/232 |
| 5,782,865 | A | 7/1998 | Grotz .................... 606/72 | 6,059,885 | A | 5/2000 | Ohashi et al. ............. 118/730 |
| 5,791,899 | A | 8/1998 | Sachdeva ................ 433/173 | 6,068,648 | A | 5/2000 | Cole et al. ................ 606/232 |
| 5,792,152 | A | 8/1998 | Klein et al. ............... 606/144 | 6,083,243 | A | 7/2000 | Pokropinski et al. ......... 606/230 |
| 5,792,153 | A | 8/1998 | Swain et al. .............. 606/144 | 6,085,690 | A | 7/2000 | Mizuno ................. 118/723 E |
| 5,792,272 | A | 8/1998 | van Os et al. ............ 118/723 R | 6,086,608 | A | 7/2000 | Elk et al. ................. 606/232 |
| 5,797,927 | A | 8/1998 | Yoon .................... 606/144 | 6,096,051 | A | 8/2000 | Kortenbach et al. ......... 606/144 |
| 5,797,963 | A | 8/1998 | McDevitt ................ 606/232 | 6,102,934 | A | 8/2000 | Li ....................... 606/232 |
| 5,810,848 | A | 9/1998 | Hayhurst ................. 606/144 | 6,113,078 | A | 9/2000 | Rock .................... 261/21 |
| 5,810,854 | A | 9/1998 | Beach ................... 606/232 | 6,114,227 | A | 9/2000 | Leksell et al. ............. 438/584 |
| 5,814,052 | A | 9/1998 | Nakao et al. .............. 606/148 | 6,117,160 | A | 9/2000 | Bonutti ................. 606/215 |
| 5,814,071 | A | 9/1998 | McDevitt et al. ........... 606/232 | 6,117,161 | A | 9/2000 | Li ....................... 606/232 |
| 5,814,072 | A | 9/1998 | Bonutti ................. 606/232 | 6,132,512 | A | 10/2000 | Horie et al. ............... 118/715 |
| 5,824,158 | A | 10/1998 | Takeuchi et al. ....... 118/723 IR | 6,143,004 | A | 11/2000 | Davis et al. ............... 606/144 |
| 5,827,370 | A | 10/1998 | Gu ...................... 118/715 | 6,146,386 | A | 11/2000 | Blackman ............... 606/103 |
| 5,843,111 | A | 12/1998 | Vijfvinkel ............... 606/171 | 6,146,406 | A | 11/2000 | Shluzas et al. ............. 606/232 |
| 5,849,004 | A | 12/1998 | Bramlet ................. 606/232 | 6,149,669 | A | 11/2000 | Li ....................... 606/232 |
| 5,851,294 | A | 12/1998 | Young et al. ............. 118/715 | 6,156,039 | A | 12/2000 | Thal ..................... 606/72 |
| 5,860,978 | A | 1/1999 | McDevitt et al. ........... 606/72 | 6,156,056 | A | 12/2000 | Kearns et al. ............. 606/232 |
| 5,860,991 | A | 1/1999 | Klein et al. ............... 606/144 | 6,159,235 | A | 12/2000 | Kim ..................... 606/232 |
| 5,860,992 | A | 1/1999 | Daniel et al. .............. 606/145 | 6,162,537 | A | 12/2000 | Martin et al. ............. 428/373 |
| 5,868,789 | A | 2/1999 | Heubner ................. 606/232 | 6,171,317 | B1 * | 1/2001 | Jackson et al. ............ 606/148 |
| 5,879,372 | A | 3/1999 | Bartlett ................. 606/232 | 6,174,324 | B1 | 1/2001 | Egan et al. ............... 606/232 |

| | | | |
|---|---|---|---|
| 6,187,101 B1 | 2/2001 | Yoshizawa | 118/718 |
| 6,197,119 B1 | 3/2001 | Dozoretz et al. | 118/715 |
| 6,200,329 B1 | 3/2001 | Fung et al. | 606/232 |
| 6,200,893 B1 | 3/2001 | Sneh | 438/685 |
| 6,206,895 B1 | 3/2001 | Levison | 606/144 |
| 6,217,592 B1 | 4/2001 | Freda et al. | 606/145 |
| 6,228,096 B1 | 5/2001 | Marchand | 606/139 |
| 6,241,736 B1 | 6/2001 | Sater | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz | 606/232 |
| 6,305,314 B1 | 10/2001 | Sneh et al. | 118/723 R |
| 6,312,526 B1 | 11/2001 | Yamamuka et al. | 118/720 |
| 6,315,781 B1 | 11/2001 | Reinhardt et al. | 606/108 |
| 6,319,252 B1 | 11/2001 | McDevitt et al. | 606/60 |
| 6,319,269 B1 | 11/2001 | Li | 606/232 |
| 6,319,271 B1 | 11/2001 | Schwartz et al. | 606/232 |
| 6,328,758 B1 | 12/2001 | Tornier et al. | 606/232 |
| 4,444,812 A1 | 2/2002 | Chen et al. | 216/60 |
| 6,344,151 B1 | 2/2002 | Chen et al. | 216/60 |
| 6,355,053 B1 | 3/2002 | Li | 606/232 |
| 6,409,743 B1 | 6/2002 | Fenton | 606/232 |
| 6,426,307 B2 | 7/2002 | Lim | 438/778 |
| 6,436,109 B1 | 8/2002 | Kontes | 606/148 |
| 6,444,039 B1 | 9/2002 | Nguyen | 118/715 |
| 6,451,030 B2 | 9/2002 | Li et al. | 606/139 |
| 6,464,713 B2 | 10/2002 | Bonutti | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,503,330 B1 | 1/2003 | Sneh et al. | 118/715 |
| 6,517,542 B1 | 2/2003 | Papay et al. | 606/73 |
| 6,520,980 B1 | 2/2003 | Foerster | 606/232 |
| 6,524,317 B1 | 2/2003 | Ritchart et al. | 606/72 |
| 6,527,794 B1 | 3/2003 | McDevitt et al. | 606/232 |
| 6,540,770 B1 | 4/2003 | Tornier et al. | 606/232 |
| 6,551,330 B1 | 4/2003 | Bain et al. | 606/144 |
| 6,569,187 B1 | 5/2003 | Bonutti et al. | 606/232 |
| 6,575,987 B2 | 6/2003 | Gellman et al. | 606/151 |
| 6,579,372 B2 | 6/2003 | Park | 118/715 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/79 |
| 6,638,880 B2 | 10/2003 | Yamamuka et al. | 118/715 |
| 6,645,227 B2 | 11/2003 | Fallin et al. | 606/232 |
| 6,648,903 B1 | 11/2003 | Pierson, III | 606/232 |
| 6,652,561 B1 * | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | 606/232 |
| 6,668,909 B2 | 12/2003 | Bondestam et al. | 165/42 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,716,234 B2 | 4/2004 | Grafton | 606/228 |
| 6,730,613 B1 | 5/2004 | Hwang et al. | 438/758 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,890,596 B2 | 5/2005 | Sarigiannis et al. | 427/248.1 |
| 6,896,674 B1 | 5/2005 | Woloszko et al. | 606/41 |
| 6,972,027 B2 * | 12/2005 | Fallin et al. | 606/232 |
| 7,029,490 B2 | 4/2006 | Grafton | 606/228 |
| 7,083,638 B2 | 8/2006 | Foerster | 606/232 |
| 7,104,999 B2 | 9/2006 | Overaker | 606/142 |
| 7,329,272 B2 | 2/2008 | Burkhart et al. | 606/232 |
| 2002/0099391 A1 * | 7/2002 | Gellman et al. | 606/148 |
| 2003/0167062 A1 | 9/2003 | Gambale | 606/232 |
| 2003/0215569 A1 | 11/2003 | Mardian | 427/248.1 |
| 2004/0083959 A1 | 5/2004 | Carpenter et al. | 118/715 |
| 2004/0138706 A1 | 7/2004 | Abrams et al. | 606/232 |
| 2004/0216671 A1 | 11/2004 | Carpenter et al. | 118/715 |
| 2005/0033364 A1 | 2/2005 | Gregoire et al. | 606/232 |
| 2005/0080455 A1 | 4/2005 | Schmieding et al. | 606/232 |
| 2005/0090827 A1 | 4/2005 | Gedebou | 606/72 |
| 2005/0277986 A1 | 12/2005 | Foerster | 606/232 |
| 2006/0004364 A1 | 1/2006 | Green et al. | 606/72 |
| 2006/0079904 A1 | 4/2006 | Thal | 606/72 |
| 2006/0271060 A1 | 11/2006 | Gordon | 606/232 |
| 2006/0271105 A1 | 11/2006 | Foerster | 606/232 |
| 2006/0293710 A1 | 12/2006 | Foerster | 606/72 |
| 2007/0142838 A1 | 6/2007 | Jordan | 606/75 |

FOREIGN PATENT DOCUMENTS

| | | |
|---|---|---|
| DE | 042 35 602 A1 | 4/1994 |
| DE | 196 28 909 A1 | 1/1998 |
| EP | 0 535 906 A2 | 4/1993 |
| EP | 0 571 686 A1 | 12/1993 |
| EP | 0 611557 | 8/1994 |
| EP | 1 072 234 A2 | 1/2001 |
| EP | 1 072 237 A1 | 1/2001 |
| FR | 2777442 | 10/1999 |
| FR | 2777447 | 10/1999 |
| JP | 02-046723 A | 2/1990 |
| JP | 2286468 | 11/1990 |
| JP | 8-52154 | 2/1996 |
| JP | 02-371361 | 12/2002 |
| WO | 91/06247 | 5/1991 |
| WO | 95/06439 | 3/1995 |
| WO | 95/025469 | 9/1995 |
| WO | 96/17544 | 6/1996 |
| WO | 98/07374 | 2/1998 |
| WO | 99/22648 | 5/1999 |
| WO | 99/53843 | 10/1999 |
| WO | 99/53844 | 10/1999 |
| WO | 02/21997 | 3/2002 |
| WO | 03/049620 | 6/2003 |
| WO | 04/082724 | 9/2004 |

OTHER PUBLICATIONS

PCT Search Report and Written Opinion for PCT/US06/21125 6pgs, Mailed May 22, 2008.
PCT International Search Report for PCT/US01/21905 3pgs, Mailed Jan. 22, 2002.
PCT International Preliminary Examination Report for PCT/US01/21905 3pgs, Oct. 17, 2003.
PCT International Search Report for PCT/US01/17689 3pgs, Mailed Dec. 19, 2001.
PCT International Preliminary Report for PCT/US01/17689 15pgs, Feb. 9, 2003.
PCT International Search Report for PCT/US02/17493 1pg, Mailed Mar. 27, 2003.
PCT International Preliminary Examination Report for PCT/US02/17493 4pgs, Sep. 8, 2003.
PCT International Search Report for PCT/US02/41018 2pgs, Mailed Jun. 5, 2003.
PCT International Preliminary Examination Report for PCT/US02/41018 3pgs, Feb. 22, 2004.
PCT International Search Report for PCT/US02/04231 1pg, Mailed Aug. 14, 2002.
PCT International Preliminary Examination Report for PCT/US02/04231 3pgs, Nov. 13, 2002.
PCT International Search Report for PCT/US03/35695 1pg, Mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
PCT International Search Report for PCT/US02/38632 2 pgs, Mailed May 16, 2003.

PCT International Preliminary Examination Report for PCT/US02/38632 3pgs, Jul. 23, 2004.

European Search Report for EP02791363 4pgs, Mailed Mar. 5, 2007.

UK Search Report for GB 0816111.9 3pgs, Dec. 16, 2008.

* cited by examiner

Fig 8.

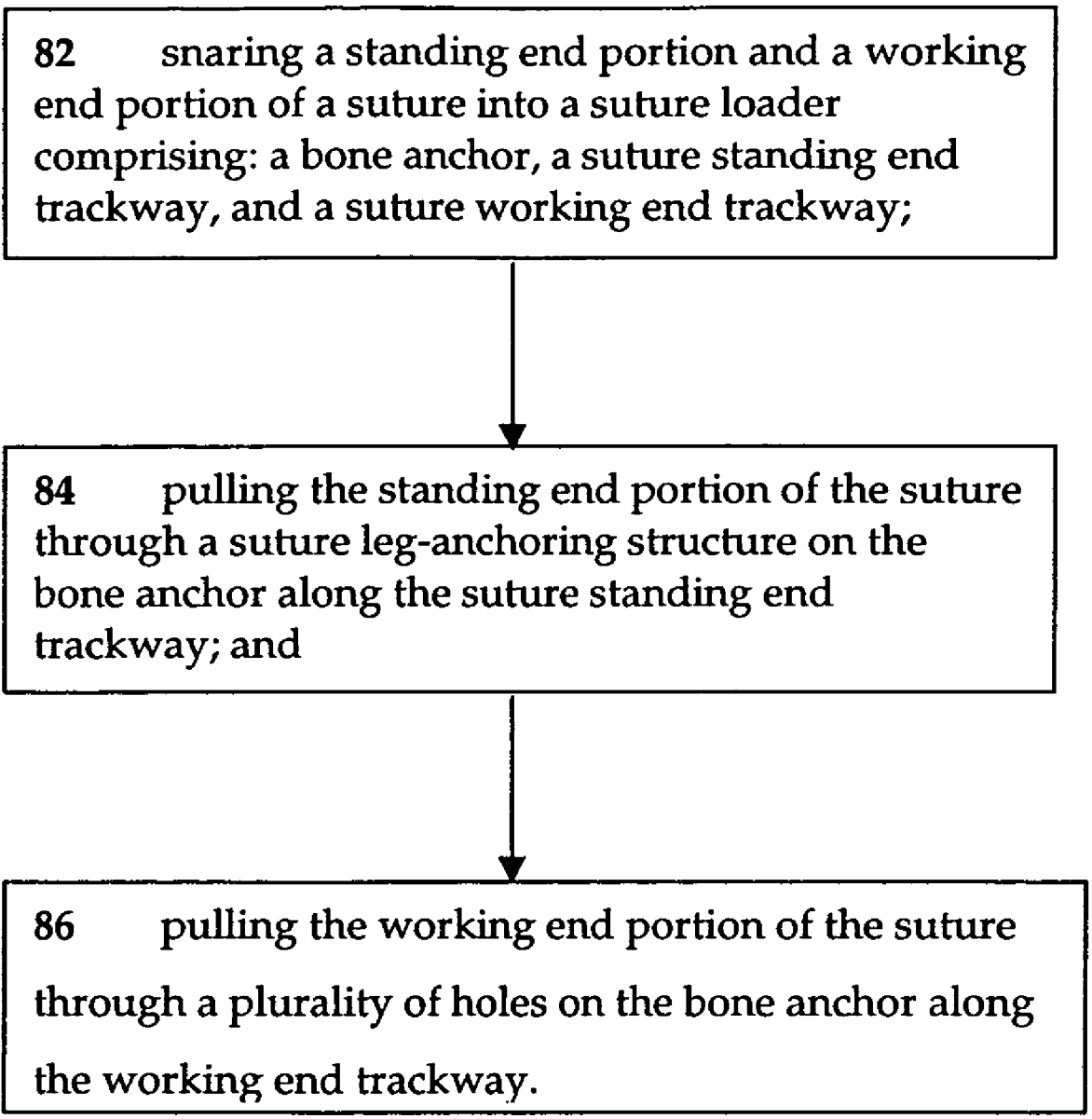

82   snaring a standing end portion and a working end portion of a suture into a suture loader comprising: a bone anchor, a suture standing end trackway, and a suture working end trackway;

84   pulling the standing end portion of the suture through a suture leg-anchoring structure on the bone anchor along the suture standing end trackway; and 86   pulling the working end portion of the suture through a plurality of holes on the bone anchor along the working end trackway.

92 suturing the tissue to obtain a standing end portion and a working end portion of suture;

94 pulling the standing end portion along a first suture trackway in a suture loader apparatus to form a first suture knot on a bone anchor disposed in the suture loader apparatus;

96 pulling the working end portion of the suture along a second suture trackway in the suture loader apparatus to cinch the suture on the anchor; and 98 deploying the anchor in the bone

BONE ANCHOR SUTURE-LOADING SYSTEM, METHOD AND APPARATUS

FIELD OF INVENTION

This invention pertains to a bone anchor suture-loading system, in particular a system, method and apparatus for automatically threading, knotting and trimming a suture onto a bone anchor, and the use thereof.

BACKGROUND

Connective tissue such as ligaments and tendons can tear and detach from the bone and muscle to cause pain and disability. One such tissue is the acetabular labrum in the shoulder which, if torn from its associated bone or muscle, will cause pain and inability to elevate and rotate the arm. Complete separation of the tissue from the bone or muscle can occur if the body is subjected to gross trauma, but the separation can also start from a small lesion on the tissue, the bone or muscle due to aging and other factors.

A detached connective tissue can surgically be reattached to the bone and muscle by an "open" procedure that involves making an incision into the body and reconnecting tissue to the bone and muscle. In one such procedure, the muscle is completely detached from the tissue and bone and the bone is debrided to match the edge of tissue at the tissue/bone reattachment location. The bone is also abraded or notched at the reattachment location to expedite healing. To reattach the tissue to the bone, a series of small diameter holes referred to as transosseous tunnels are punched through the bone over a distance of about 2 cm to 3 cm on the bone. One end of the suture is attached to the muscle and the other end is attached to the bone by threading the suture through the transosseous tunnels and tying the suture to intact bone between two successive tunnels; thereafter, the incision is closed.

As used herein the portion of the suture attached to the tissue or bone is referred to as the "standing end"; the end that extends towards the handler, or is manipulated by the handler, is referred to as the "working end"; the distal end of the implant or suture is that portion located away from the handler; and the proximal end is located next to or near the handler.

As will be appreciated, because the open procedure detaches the muscle and abrades the bone, the patient may experience discomfort and a relatively long recovery time.

In an alternative procedure that reduces trauma to the patient, the reattachment is done arthroscopically. In an arthroscopic procedure the surgeon reconnects the tissue to the bone by working through a small trocar portal into the body to reattach the tissue. In one arthroscopic procedure, rather than using transosseous tunnels to thread the suture through the bone, which is difficult to achieve arthroscopically, the tissue is connected to the bone by attaching one end of the suture to the tissue, securing the other end of the suture in a bone anchor, and embedding the anchor in the bone at the appropriate location thereby reattaching the tissue to the bone.

Although arthroscopic procedures are less invasive than open procedures, an arthroscopic procedure is not always the procedure used. One reason is that arthroscopic suturing of the tissue requires a high level of skill not possessed by all surgeons. Also, arthroscopic suturing of the tissue is clumsy and time consuming and only the simplest stitch patterns can be utilized. Additionally, tying a suture knot arthroscopically is challenging because it is difficult to judge the tightness of the suture. Also, the tension on the suture is not easily adjustable arthroscopically once the knot is formed. Further, in arthroscopic suturing, the knot required to tie the tissue may end up on top of the tissue in the form of a knot bundle, which is undesirable because of the potential for postoperative irritation when the muscle is exercised.

U.S. patent application Ser. No. 10/942,275 by Fallin et al. ("Fallin") discloses a line lock threading system useable for selectively adjusting and/or tying off a line using a line lock. The system includes a cartridge that includes a retention feature shaped to retain the line lock. The line lock comprises a body that bounds a plurality of passageways through which the line is treaded. The system also includes a treading feature shaped to facilitate insertion of the line through the passageways of the line lock.

U.S. Pat. No. 6,652,561 to Tran ("Tran") assigned to the present applicant and hereby incorporated by reference herein for all purposes discloses an embeddable bone anchor that eliminates the need to tie a knot on the tissue, while allowing for adjusting the tension on the suture and the tissue. The suture is threaded through holes in the anchor such that on pulling on the suture, the suture and tissue are locked to the anchor without a knot on the tissue. A deployable structure on the anchor embeds the anchor body in the bone and resist pullout.

Co-pending U.S. patent application Ser. No. 11/375,691 by Forester et. al ("Forester et. al"), assigned to the present applicant and incorporated herein by reference for all purposes, discloses a suture lock and bone anchor that cinches the suture and tissue to the anchor without a knot on the tissue. As is illustrated in FIGS. 1 and 2 herein, a suture loop (12) is formed on the anchor (10) by fastening a first leg (12a) of the suture onto the distal end of the anchor, and threading the tail (16) of the suture through a plurality of holes (14a, 14b, 14c) in the anchor to form a second suture leg (12b) on the anchor. On pulling on the tail or working end of the suture (16), the suture tightens on the anchor to cinch the loop (12) and tissue (18) to the anchor, without a knot on the tissue. When the anchor (10) is embedded in the bone (20) the fixed leg (12a), which is the standing end of the suture, is positioned distally on the anchor. Barbs (24) on the anchor assist in embedding the anchor and resisting pullout from the bone.

In procedures for reconnecting tissue to bone using anchors, there is a continuing need for systems to improve the threading of sutures to the anchors, and which avoid tying knots on the tissue. It is therefore and objective of the present invention to address these needs.

SUMMARY OF THE INVENTION

The present suture-loading system in one embodiment comprises: a bone anchor comprising a suture leg-anchoring structure and a plurality of body holes; a suture comprising a standing end portion and a working end portion; a standing end trackway to guide the standing end portion of the suture through the suture leg-anchoring structure; and a working end trackway to guide the working end portion of the suture through the body holes.

The present method of loading a suture onto a bone anchor in one embodiment comprises: snaring a standing end portion and a working end portion of a suture into a suture loader comprising a bone anchor, a suture standing end trackway, and a suture working end trackway; pulling the standing end portion of the suture through a suture leg-anchoring structure on the bone anchor along the suture standing end trackway; and pulling the working end portion of the suture through a plurality of holes on the bone anchor along the working end trackway.

The present suture loader apparatus for loading a suture on a bone anchor in one embodiment comprises: an anchor cradle adapted to receive a bone anchor; a suture trackway oriented to tie a suture knot on the bone anchor in the bone anchor cradle.

The present method of embedding tissue to bone in one embodiment comprises: suturing the tissue to obtain a standing end portion and a working end portion of suture; pulling the standing end portion along a first suture trackway in a suture loader apparatus to form a first suture knot on a bone anchor disposed in the suture loader apparatus; pulling the working end portion of the suture along a second suture trackway in the suture loader apparatus to cinch the suture on the anchor; and deploying the anchor in the bone.

Details of various embodiments of the present method, system and apparatus are illustrated and described the following Figures and specifications.

BRIEF DESCRIPTION OF THE DRAWINGS

FIG. 8 is an algorithm of the present method of loading a suture onto the bone anchor.

FIG. 9 is an algorithm of a method of embedding tissue in bone using the to present bone anchor suture-loading system.

DETAILED DESCRIPTION

Figure 1:
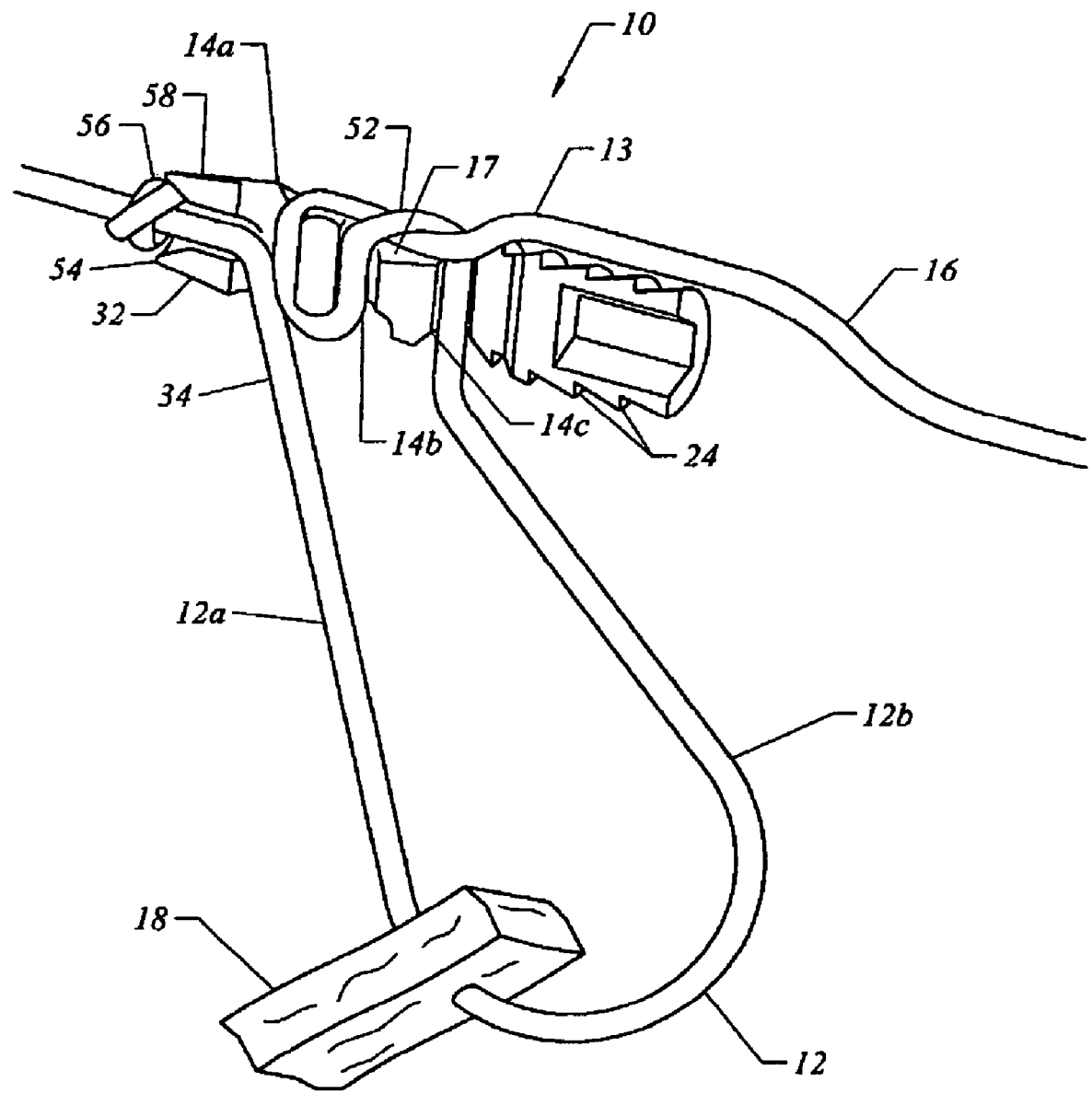
FIG. 1 is an illustration of a bone anchor with a threaded suture.
Figure 2:
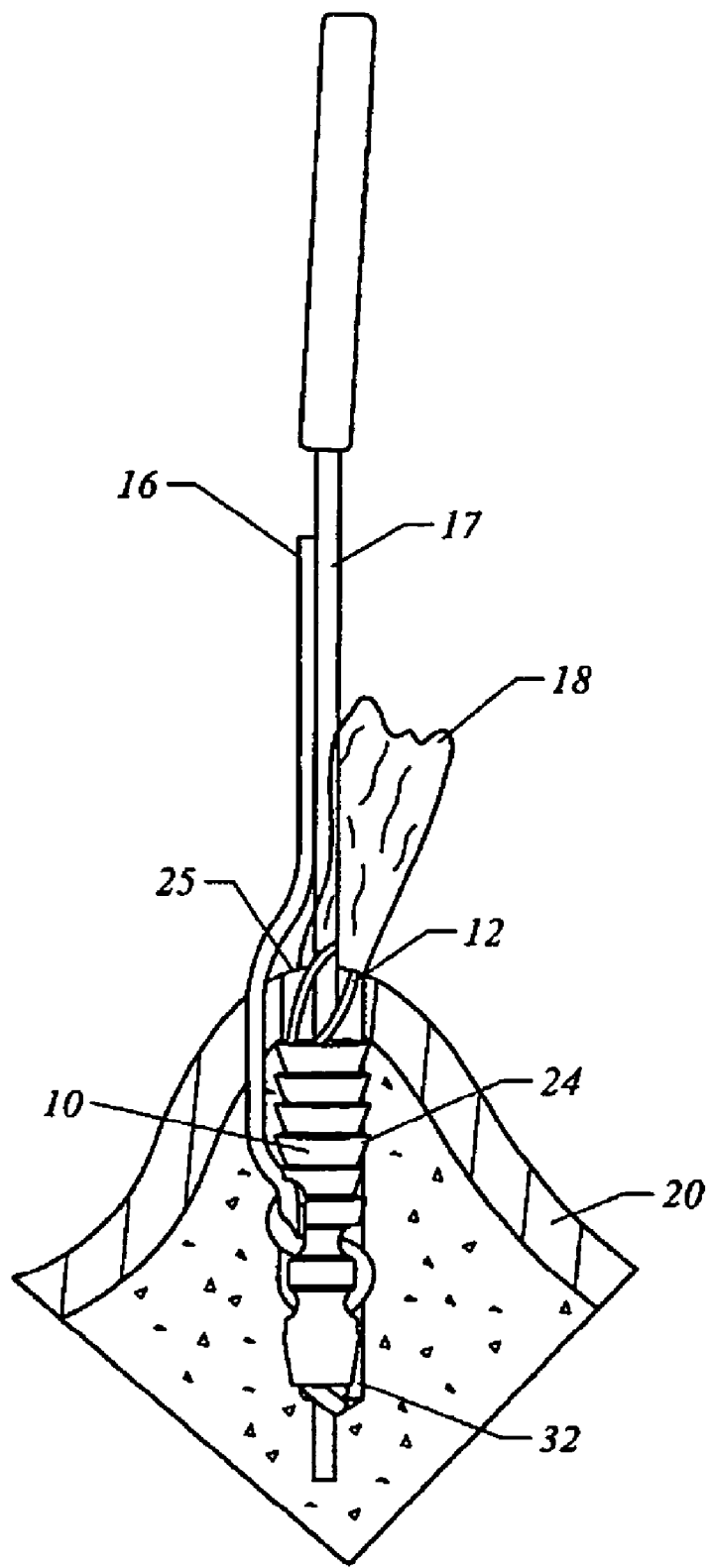
FIG. 2 is an illustration of an anchor embedded in a bone.
Figure 3:
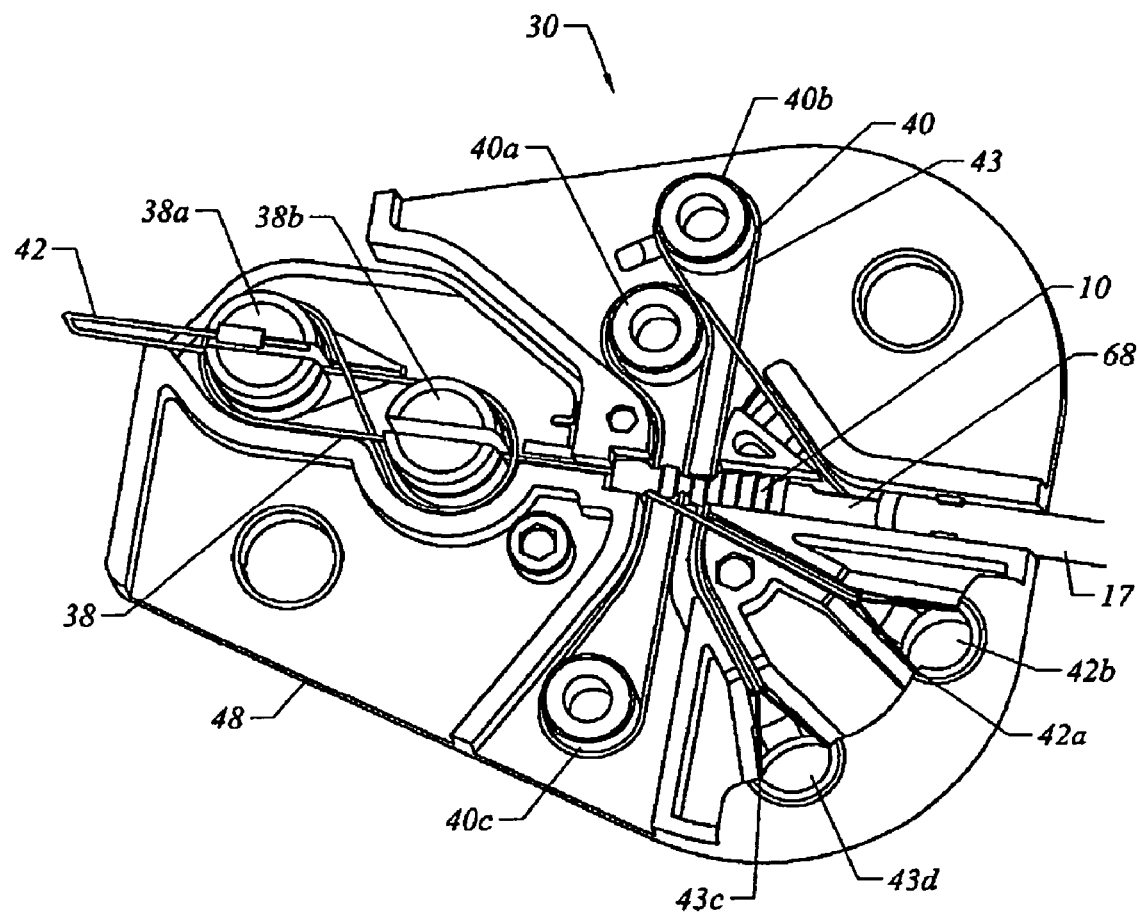
FIG. 3 is an illustration of an embodiment of the present suture-loading system preloaded with snare wires.
Figure 4:
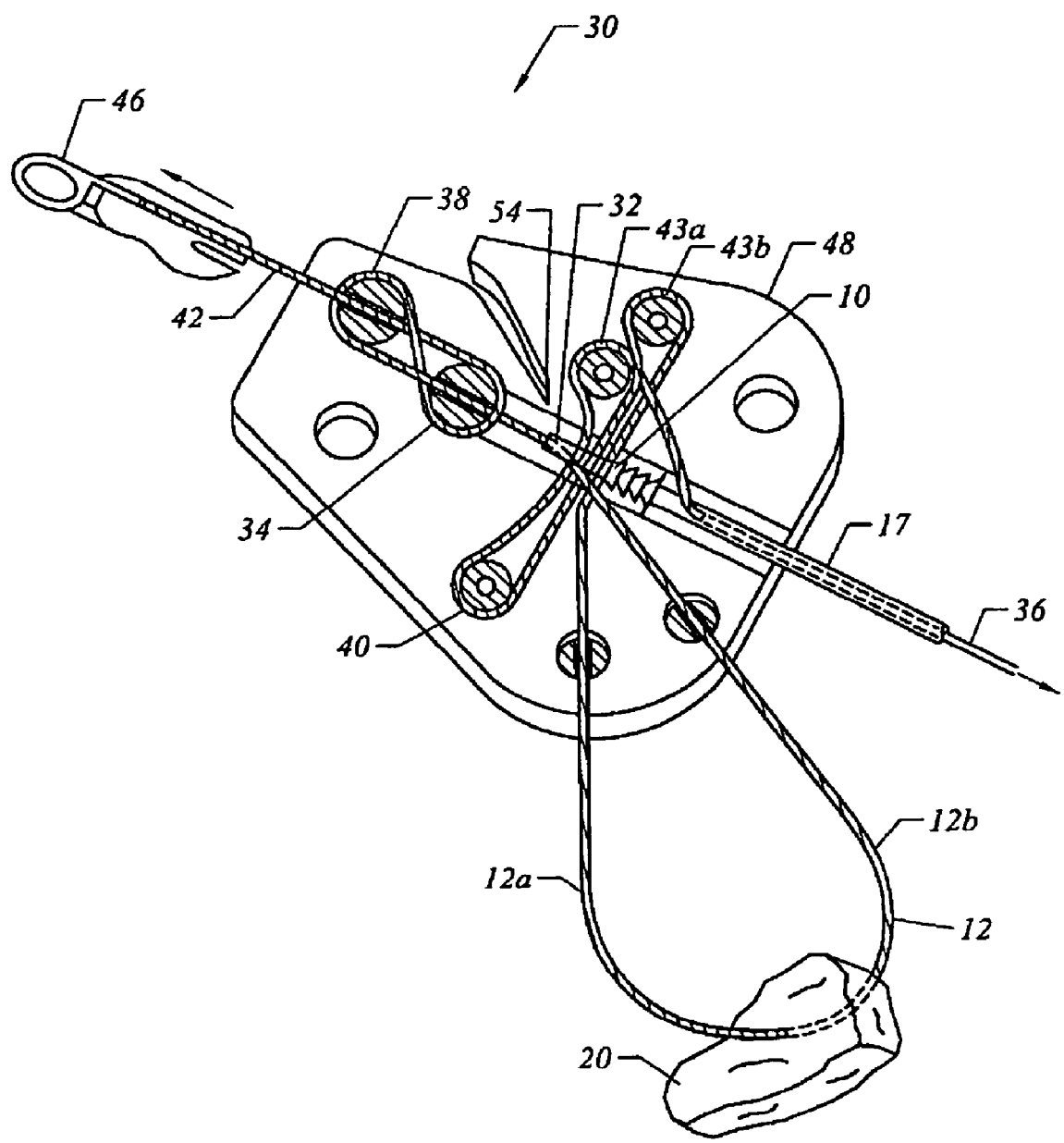
FIG. 4 is an illustration of an embodiment of the present suture-loading system loaded with a suture.
Figure 5:
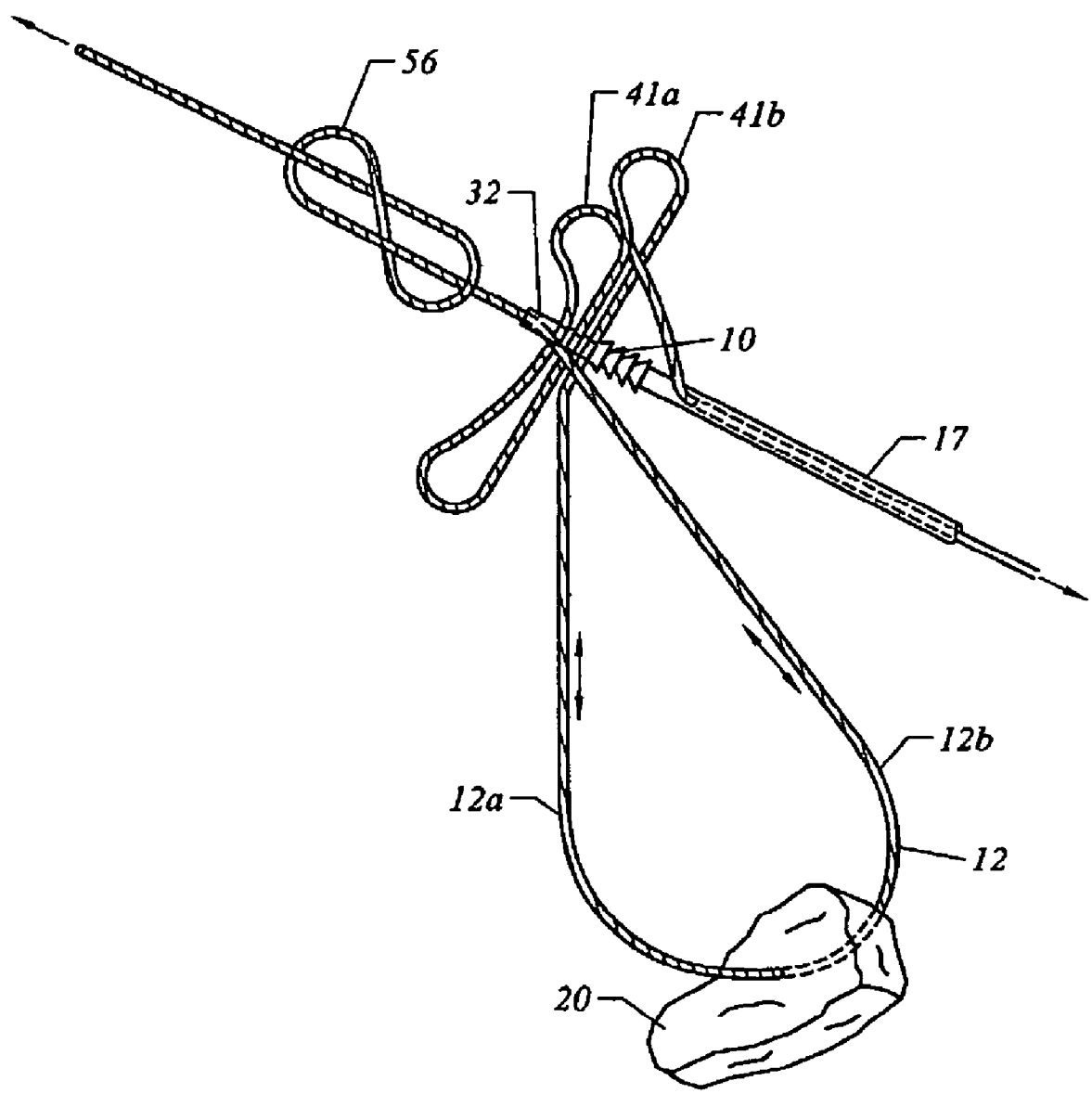
FIG. 5 is an illustration of a bone anchor loaded with a suture and removed from the present suture-loading system.
Figure 6:
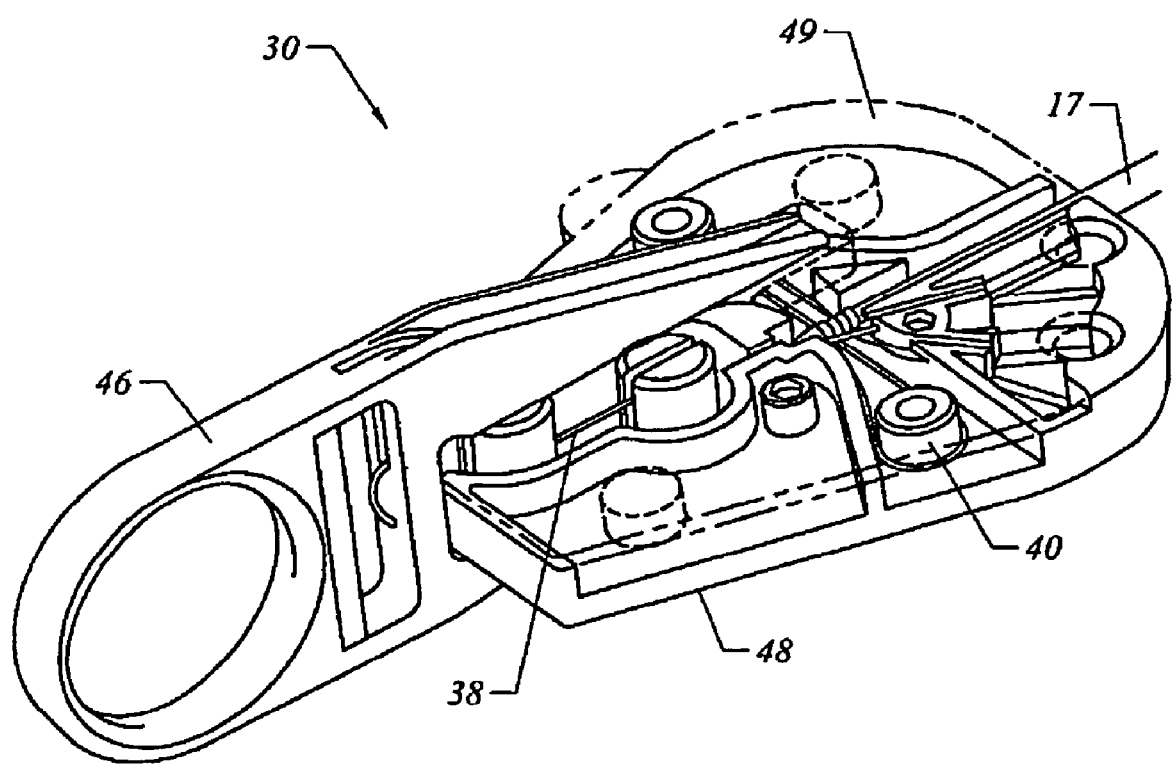
FIG. 6 is an illustration of the present suture-loading system with a lid over the base and a pull ring attached to base.
Figure 7:
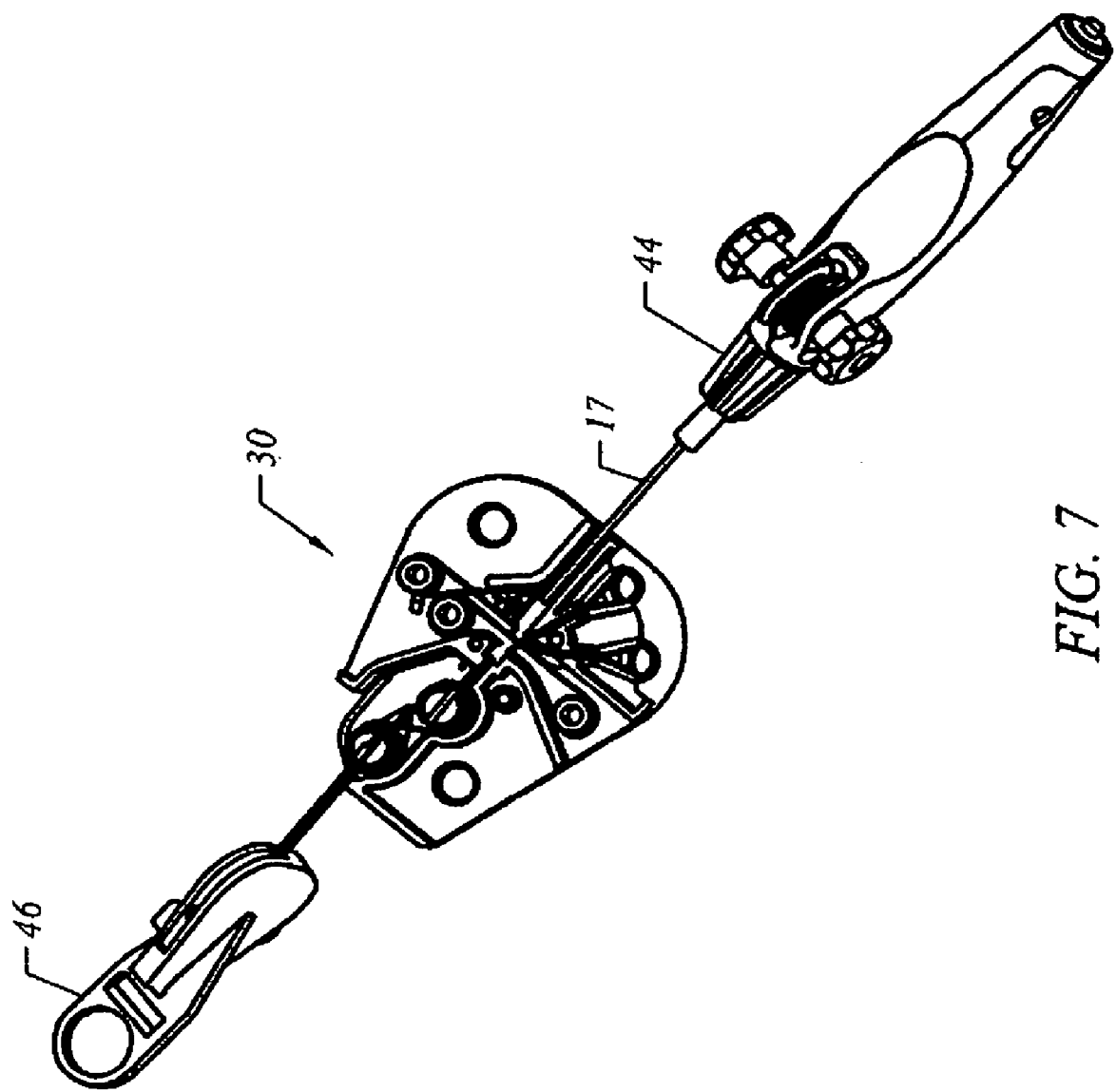
FIG. 7 is an illustration of an embodiment of the present suture-loading system including a pull ring and suture reel connected by a suture through a base.

The present suture-loading system, method and apparatus are illustrated in FIGS. 1-9. In particular, an embodiment of a bone anchor loaded with a suture in accordance with the present method and system is illustrated in FIG. 5. A cross-section of the loaded anchor is illustrated in FIG. 1. The use of the loaded anchor to reattach tissue to the bone is illustrated in FIG. 2. Snare-wires attached to the suture and loaded into trackways to pull and guide the suture through the loader are illustrated in FIGS. 3, 4, 6 and 7. Algorithms of methods of loading the suture on to the anchor, and for embedding the tissue in a bone are illustrated in FIGS. 8-9.

With reference to FIGS. 1-7, the present bone anchor suture-loading system (30) comprises several components that cooperate to load and cinch the suture to the anchor. The components include: (i) a bone anchor (10) through which holes are formed to thread, knot and cinch the suture to the anchor; (ii) embedding structural features (24) on the bone anchor to facilitate embedding the anchor in the bone; (iii) a suture (12) comprising a standing end portion (34) and a working end portion (36) for securing soft tissue to the anchor; (iv) a suture standing end trackway (38) pre-loaded with a snare-wire (42b) to snare and pull the standing end portion of the suture through the anchor to form a knot (56) on the suture against the anchor; and (iv) a suture working end trackway (40) pre-loaded with a snare-wire (42a) to snare and pull the working end of the suture through the anchor to form a cinch point (52) on the anchor.

Optionally the system includes a pull-ring (46) to aid in pulling the snare wire (42) and standing end of the suture (34) through the standing end trackway (38); a suture reel (44) to aid in pulling the snare wire (43) and the working end of suture (36) through the working end trackway (40); and a cutting element or blade (54) to trim excess suture and cut the suture from the snare wires after the suture is threaded in the trackways (38, 40). In various embodiments the system is housed on a base (48) with a detachable lid (49) covering the base, and all the components can be formed from plastics and metal parts. Preferred materials include polycarbonates, nylon, zytel, and similar plastics. An overall size of the base and the lid is approximately 2 inches×2 inches×⅜ inches thick, however the size can be modified as needed to accommodate different anchors and the suture pattern desired on the anchor.

With reference to FIG. 1, an anchor that illustrates the use of the present suture loading system is described in co-pending U.S. patent application Ser. No. 11/375,691 by Forester et. al, herein incorporated by reference. In one embodiment the anchor (10) comprises: a body structure (13) having a plurality of body holes (14a, 14b, 14c) adapted to thread the working end of the suture (12, 16) through the anchor to form a cinch point (52), and the standing end of the suture to form a knot (56) on the distal end of the anchor (10); a suture leg-anchoring structure (32) adapted to fasten the standing end of the suture (12a, 34) onto the anchor; and a bone embedding structure (24) adapted to embed the anchor in the bone (20).

With reference to FIG. 1, the body holes (14a, 14b, 14c) extend through the anchor and are offset from each other relative to the longitudinal axis of the anchor to facilitate forming cinch point (52) on the working end of the suture against the anchor. As is illustrated in FIG. 1, the surface on the anchor under the cinch point (52) is flattened (17) to seat and reduce the profile of the cinch on the anchor. The diameter of the body holes is sized to accommodate one or more strands of suture.

With reference to FIG. 1, a suture leg-anchoring hole (54) that extends through the suture leg-anchoring structure (32) allows for passing the standing end of the suture (34) through the distal end of the anchor to fasten the suture to the anchor by a retaining knot (56). To ensure that the suture knot (56) is securely attached over the suture-anchoring hole, the cross-section of the knot (56) is made larger than the cross-section of the suture-anchoring hole. As will be appreciated by one ordinarily skilled in the art, the standing end of the suture can also be retained on the suture leg-anchoring structure by attaching the suture onto a structure disposed outside of the sure anchoring hole.

With reference to FIGS. 1 and 2, to facilitate retaining the anchor in bone the anchor is provided with a bone-embedding structure (24) located proximal to the suture leg-anchoring structure (32). In one embodiment the bone-embedding structure (24) comprises a plurality of barbs oriented towards the distal end of the anchor. As is illustrated in FIGS. 1 and 2, the barbed structures taper towards the distal end of the anchor to resist proximal pullout of the anchor from the bone (20).

With reference to FIGS. 3-6, the present suture standing end trackway (38) in one configuration comprises removable pins (38a, and 38b) located in the base (48) such that a pre-threaded snare-wire (42) can be configured around and through the pins into a pattern that can be transferred to the suture by snaring and pulling the suture through the trackway (38) and removing the pins. In a particular embodiment illustrated in FIGS. 4 and 5, the snare wire is pre-configured into a figure-8 pattern that becomes a figure-8 knot (56) on the suture when the pins are removed. The knot (56) is tightened by pulling on the suture both sides of the knot. In one embodiment, the distal end of the suture is attached to pull-ring (46) to tighten the knot. After the knot is tightened excess suture is trimmed by routing the suture over the cutting blade (54).

With reference to FIG. 3-6, the present suture working end trackway (40) in one configuration comprises posts (40a, 40b, 40c) located in the base (48) such that a pre-threaded snare-wire (43) can be configured around the posts into a pattern that can be transferred to the suture by snaring and pulling the suture through body holes (14a, 14b, 14c) in the anchor (10) and through the trackway (40). In an embodiment illustrated in FIGS. 4 and 5, the snare wire is pre-configured into two intertwined loops (43a and 43b) that will form a cinched point (52) when the anchor is removed form the anchor cradle (68) and the working end of the suture (36) is tensioned. In one embodiment, the proximal end of the suture is attached to suture reel (44) that can be operated to gradually cinch the suture on the anchor (10) and fix the size of the loop (12). As will be appreciated by one ordinarily skilled in the art, to cinch the tissue to the anchor on the loop, the suture is attached to the tissue before the standing and working ends of the suture are snared into the trackways (38, 40) by the pull-ring (46) and the suture reel (44). As is illustrated in FIG. 3, each of the snare wires (42, 43) comprise a loop (42a, 43c) at the end of the snare wire to snag the working end (36) and standing end (34) of the suture. In one embodiment the loops (42a, 43c) are stretched open to snag the ends of the suture (12a, 12b) by looping the ends concentrically around a pair of holes (42b, 43c) in the base (48). In one embodiment as illustrated in FIG. 2-4 the suture reel (44) comprises a handle (17) useable to guide the loaded anchor into hole (25) in the bone (20) to embed the anchor (10) and tissue (18) in the bone. After inserting the anchor in the hole (20) as is illustrated in FIG. 2, excess suture tail (16) can be is cutoff by the surgeon. In various embodiments the present suture loading system is useable to load a suture including braided and monofilament sutures.

With reference to FIG. 8, the present suture loading system can be used to load a suture onto a bone anchor by a series of steps, as follows: (82) snaring a standing end portion (34) and a working end portion (36) of the suture (12) into a suture loader (30) comprising: a bone anchor (10), a suture standing end trackway (38), and a suture working end trackway (40); (84) pulling the standing end portion of the suture through a suture leg-anchoring structure (32) on the bone anchor (10) along the suture standing end trackway (38); and (86) pulling the working end portion (36) of the suture through a plurality of holes (14a, 14b, 14c) on the bone anchor along the working end trackway (40). These steps can be implemented as described above on the present apparatus and system.

With reference to FIG. 9, the present suture loading system can be used for embedding tissue to bone by a series of steps, as follows: (92) suturing the tissue to obtain a standing end portion and a working end portion of suture; (94) pulling the standing end portion along a first suture trackway in a suture loader apparatus to form a first suture knot on a bone anchor disposed in the suture loader apparatus; (96) pulling the working end portion of the suture along a second suture trackway in the suture loader apparatus to cinch the suture on the anchor; and (98) deploying the anchor in the bone. These steps can be implemented as described above on the present apparatus and system.

Accordingly, as illustrated for example in FIG. 5, with the present system and method a suture can be loaded onto an anchor (10) such that a knot (56) is formed on the standing end of the suture (32), while the working end of the suture is cinched (52) to form a loop (12) attached to a tissue (18). Excess lengths of suture can be trimmed off after the anchor is loaded, and the loaded anchor removed from the system by separating the lid (49) from the base (48), without entangling the suture. Thus loaded, the anchor can be imbedded an a bone to reattach a connective tissue.

By the present description and Figures it is to be understood that the terms used herein are descriptive rather than limiting, and that changes, modifications, and substitutions may be made without departing from the scope of the invention. Therefore the invention is not limited to the embodiments described herein, but is defined by the scope of the appended claims.

What is claimed is:

1. An bone anchor suture-loading system comprising:
   a bone anchor comprising a suture leg-anchoring structure and a plurality of body holes;
   a suture comprising a standing end portion and a working end portion;
   a standing end trackway to guide the standing end portion of the suture through the suture leg-anchoring structure;
   a working end trackway to guide the working end portion of the suture through the body holes,
   wherein the standing end trackway and the working end trackway are housed on a base, and wherein the bone anchor is removable from the base; and
   a snare-wire disposed in the standing end trackway and the working end trackway, the snare-wire slidable along a path disposed on the base and configured to pass through the bone anchor.

2. The bone anchor suture-loading system of claim 1, wherein the bone anchor comprises a bone-embedding structure adapted to embed the anchor in the bone.

3. The bone anchor suture-loading system of claim 2, wherein the bone-embedding structure comprises a plurality of embedding barbs disposed on the bone anchor.

4. The bone anchor suture-loading system of claim 1, wherein the suture leg-anchoring structure comprises a leg-anchoring hole adapted to secure the standing end portion of the suture by a knot on the suture.

5. The bone anchor suture-loading system of claim 4, wherein the leg-anchoring hole defines a shoulder for fastening the suture knot.

6. The bone anchor suture-loading system of claim 1, wherein the standing end trackway comprises a plurality of pins positioned on the base to configure a knot on the standing end portion of the suture.

7. The bone anchor suture-loading system of claim 6, wherein the pins are removable from the base to form the knot.

8. The bone anchor suture-loading system of claim 1, wherein the standing end portion of the suture is attached to a pull-ring to pull the suture at least partly through the standing end trackway.

9. The bone anchor suture-loading system of claim 1, wherein the working end trackway comprises a plurality of posts positioned on the base to configure a cinchable suture loop on the standing end portion of the suture.

10. The bone anchor suture-loading system of claim 1, wherein the working portion of the suture is attached to a suture reel to pull the suture at least partly through working end trackway.

11. The bone anchor suture-loading system of claim 1, wherein the snare-wire comprises a loop at each end of the snare-wire to snag the working end and standing end portions of the suture.

12. The bone anchor suture-loading system of claim 11, wherein each of the snare loops is positioned concentric to a first and a second hole formed in the base.

13. The bone anchor suture-loading system of claim 12, wherein the first and second holes are sized to receive respectively the working end and standing end of the suture.

14. The bone anchor suture-loading system of claim 1, wherein the suture is selected from the group consisting of braided suture and a monofilament suture.

15. The bone anchor suture-loading system of claim 1, wherein the base comprises a cutting element to trim excess portions of the suture.

16. The bone anchor suture-loading system of claim 1, wherein a lid on the base encloses the anchor, standing end trackway and the working end trackway.

17. The bone anchor suture-loading system of claim 16, wherein the base and lid are detachable from each other to expose the threaded implant without entanglement.

18. The bone anchor suture-loading system of claim 16, wherein the base and lid are comprised of material selected from the group consisting of metal, polycarbonate, nylon, zytel, and other plastics.

19. The bone anchor suture-loading system of claim 1, wherein the snare-wire is configured into two intertwined loops, wherein the two intertwined loops will form a suture cinched point on the bone anchor.

* * * * *